(12) United States Patent
Maruo et al.

(10) Patent No.: US 7,333,841 B2
(45) Date of Patent: Feb. 19, 2008

(54) METHOD AND DEVICE FOR CALCULATING A BIOLOGICAL COMPONENT DENSITY OF A SUBJECT

(75) Inventors: Katsuhiko Maruo, Itami (JP); Mitsuhiro Tsurugi, Ashiya (JP)

(73) Assignee: Matsushita Electric Works, Ltd., Osaka (JP)

( * ) Notice: Subject to any disclaimer, the term of this patent is extended or adjusted under 35 U.S.C. 154(b) by 615 days.

(21) Appl. No.: 10/478,276

(22) PCT Filed: Nov. 14, 2002

(86) PCT No.: PCT/JP02/11871

§ 371 (c)(1), (2), (4) Date: Nov. 20, 2003

(87) PCT Pub. No.: WO03/041582

PCT Pub. Date: May 22, 2003

(65) Prior Publication Data

US 2004/0142402 A1  Jul. 22, 2004

(30) Foreign Application Priority Data

Nov. 15, 2001 (JP) ............................. 2001-350746

(51) Int. Cl.
*A61B 5/00* (2006.01)
(52) U.S. Cl. ....................................... 600/316; 600/310
(58) Field of Classification Search ................ 436/14; 600/316, 310, 322, 473

See application file for complete search history.

(56) References Cited

U.S. PATENT DOCUMENTS 5,460,177 A * 10/1995 Purdy et al. ................ 600/436

(Continued)

FOREIGN PATENT DOCUMENTS

JP  9-215679 A1  8/1997

(Continued)

OTHER PUBLICATIONS

Fruhstorfer et al. "Thickness of the Strateum Corneum of the Volar Fingertips" Clinical Anatomy (2000) vol. 13, pp. 429-433.*

(Continued)

*Primary Examiner*—Eric F Winakur
(74) *Attorney, Agent, or Firm*—Cheng Law Group PLLC

(57) ABSTRACT

A method for calculating a biological component density of this invention comprises steps of irradiating a light of NIR spectrum to a skin of a subject, receiving the light of NIR reflected from the skin to obtain NIR spectrum data thereof, and substituting the NIR spectrum data into a predetermined calibrating equation to obtain a biological component density of the subject such as glucose density. This invention is characterized by preparing a plurality of the calibrating equations which are different from each other and are specific to each of plural groups which are classified in terms of a skin thickness parameter indicative of a skin thickness with respect to individuals of a species to which the subject belongs, determining the skin thickness parameter of the subject with a non-invasive technique and identifying the group of the subject in accordance with the determined skin thickness parameter, and deriving one of the calibrating equations in match with the identified group in order to calculate the biological component density of the subject.

7 Claims, 12 Drawing Sheets

U.S. PATENT DOCUMENTS 5,725,480 A    3/1998 Oosta et al.
6,512,937 B2 * 1/2003 Blank et al. ................ 600/322

FOREIGN PATENT DOCUMENTS

| JP | 2000-131322 A1 | 5/2000 |
| JP | 2000-237195 A1 | 9/2000 |
| JP | 2001-212116 A1 | 8/2001 |
| WO | WO-00/42907 A1 | 7/2000 |
| WO | WO01/95800 * | 12/2001 |

OTHER PUBLICATIONS

International Search Report for PCT/JP02/11871 mailed on Feb. 4, 2003.

* cited by examiner

METHOD AND DEVICE FOR CALCULATING A BIOLOGICAL COMPONENT DENSITY OF A SUBJECT

TECHNICAL FIELD

The present invention relates to a method and a device for calculating a biological component density of a subject and, more particularly, it relates to a method and a device for calculating a biological component density for calculating a chemical component in body tissue by spectrochemical analysis using absorption of light in near-infrared region. Specifically, it relates to a useful method and a device to calculate glucose density in skin structure based on quantitative analysis.

BACKGROUND ART

Japanese Non-examined Patent Publication No.2000-131322 discloses a quantitative method of glucose density and a device for the method. This prior art comprises the steps of irradiating light of near infrared (hereinafter called NIR) spectrum to a skin of a subject, receiving the light of NIR reflected from the skin to obtain NIR spectrum data thereof, and substituting the NIR spectrum data into a predetermined calibrating equation to obtain glucose density of the subject. In this prior art, when a biological component density in skin structure of each subject is measured, different calibrating equations are prepared for each individual to measure it, because there are large individual differences in skin structure of human beings or living things as subjects.

However, preparing the calibrating equations for each individual or each measurement part requires to restrain people or living things as measuring objects for a long time to prepare the calibrating equations by multivariate analysis of the NIR spectrum data and an actual measurement data. Therefore, the subjects and those who prepare the calibrating equations have to have heavy burden. For this reason, it was difficult to carry out easy and correct measurement to each of subjects with big individual differences.

DISCLOSURE OF THE INVENTION

In view of the above problem, the object of the present invention is to provide a method and a device for calculating a biological component density in skin structure of subjects with large individual differences without preparing a different calibrating equation for each individual.

A method for calculating a biological component density of this invention comprises steps of irradiating a light of NIR spectrum to a skin of a subject, receiving the light of NIR reflected from the skin to obtain NIR spectrum data thereof, and substituting the NIR spectrum data into a predetermined calibrating equation to obtain a biological component density of the subject such as glucose density. This invention is characterized by preparing a plurality of the calibrating equations which are different from each other and are specific to each of plural groups which are classified in terms of a skin thickness parameter indicative of a skin thickness with respect to individuals of a species to which the subject belongs, determining the skin thickness parameter of the subject with a non-invasive technique and identifying the group of the subject in accordance with the determined skin thickness parameter, and deriving one of the calibrating equations in match with the identified group in order to calculate the biological component density of the subject.

Consequently, what is necessary is just to prepare the calibrating equations for each of the groups, not for each individual, which are classified in terms of a skin thickness parameter. So it is possible to calculate the biological component density simply and accurately to many individuals.

It is preferable that the skin thickness parameter is determined by analyzing the NIR spectrum reflected from the skin of the subject statistically. Consequently, it is possible to use the reflected NIR spectrum which is used in order to calculate the glucose density effectively to classify the subjects in terms of the skin thickness parameter without using another equipment. It is preferable to use a principal component analysis as the statistical analysis.

Instead of the statistical analysis, it is also effective that the NIR spectrum reflected from the skin of the subject is analyzed with respect to an absorption coefficient of the spectrum at a frequency at which the spectrum is expected to show specific absorption due to existence of subcutaneous fat of the individual, thereby determining the skin thickness parameter based upon the absorption coefficient. That is, it becomes possible to classify the individual easily based of the skin thickness by using the fact that the amount of the subcutaneous fat obtained by analysis of the absorption coefficient has a correlation with the skin thickness. It is preferable that the frequency at which the absorption coefficient is measured is within a range of 1700 nm to 1800 nm.

Furthermore, in a preferred embodiment of this invention, the NIR spectrum is irradiated to the skin selectively through one of a plurality of different incident paths which are spaced by different distances along a skin surface from a common reflective path through which the NIR spectrum is reflected out from the skin. The different incident paths are assigned as being specifically suitable to the groups, respectively. The NIR spectrum irradiated through one of the incident paths and reflected from the skin is analyzed to determine the skin thickness parameter, and one of the different incident paths assigned to one of the groups identified by the determined skin thickness parameter is selected. The selected incident path is made active to irradiate the NIR spectrum to the skin so as to obtain the NIR spectrum data reflected from the skin. The NIR spectrum data is processed by use of the calibrating equation specific to one of the groups determined by the skin thickness parameter. The above procedure takes it into consideration that the position of a dermal organization, which is supposed to reflect most the biological component to be calculated, changes with the skin thickness, therefore, it becomes possible to select the reflective path which certainly passes the dermal organization and calculate the correct biological component density by preparing two or more reflective paths according to the skin thickness, namely, according to the groups.

Instead of the above statistical analyzing and the above analyzing method to analyze the reflected NIR spectrum with respect to the absorption coefficient at certain frequency, the skin thickness parameter may be determined by a non-invasive technique using an ultrasound thickness gauge or an optical coherence tomography.

A device for realizing the above mentioned method comprises a light source generating a light having a NIR spectrum, an incident guide directing the light to a skin of the subject, a reflective guide directing the NIR spectrum reflected back from within the skin, a sensor receiving the NIR spectrum through the reflective guide to provide NIR data thereof, and a processing unit which substitutes the NIR data into a predetermined calibrating equation to calculate the biological component density such as glucose density of the subject. The device further includes a skin thickness memory storing a plurality of the calibrating equations which are different from each other and which are each specific to each of plural groups classified in terms of a skin thickness parameter indicative of the skin thickness with respect to individuals of a species to which the subject belongs, and a means for determining the skin thickness parameter with an non-invasive technique to identify the group of the subject in accordance with the determined skin thickness parameter. The above processing unit derives one of the calibrating equations from the skin thickness memory in match with the identified group, and calculate the biological component density of the subject.

It is preferable that the incident guide has a light projecting end adapted to be held in close proximity to the skin, and the reflective guide has a light receiving end adapted to be held in close proximity to the skin, and the light receiving end is spaced from the light projecting end by a distance of 2 mm or less across the skin. By such disposition, it becomes possible to obtain the NIR spectrum which passed and reflected subsequently the dermal organization which is supposed to reflect most the biological component to be calculated. Therefore, the measurement of the biological component density can be made accurately.

In a preferred embodiment, the incident guide and the reflective guide are made respectively by optical fibers, and they are integrated into a single probe head having an object end to which the light projecting end and the light receiving end are exposed. Consequently, the operation to the skin of the subject becomes easy.

It is also preferable that the prove includes a plurality of different incident guides and a single reflective guide, and the different incident guides have individual light projecting ends which are spaced by different distances, respectively from the light receiving end. The light source is selectively coupled with one of the different incident guides by a selector, and the NIR spectrum is irradiated through the selected incident guide to the skin, and the reflected NIR spectrum therefrom is sent out to the above sensor. The processing unit further includes a table storing a relation between each one of the groups and each one of the different incident guides and a module which analyzed the NIR data statistically based upon the NIR spectrum irradiated through one of the incident paths and received from the skin to determine the skin thickness parameter and to identify the corresponding one of the groups. The module selects from the table one of the different incident guides as corresponding to the identified group, and enables the selector to activate the selected incident guide to direct the NIR spectrum to the skin for calculation of the biological component density based upon the NIR spectrum irradiated through the selected incident path and reflected from the skin. Therefore, it becomes possible to take out the NIR spectrum which passes the dermal organization of which depth varies by the skin thickness and reflects subsequently, as effective data, and thereby, it becomes possible to measure the biological component density accurately based on the data.

It is preferable that a plurality of the incident guides are arranged around the single reflective guide and the light projecting ends are disposed coaxially around the light receiving end, on the object end of the probe head. Thereby, the NIR spectrum reflected from the skin can be directed certainly to the single light receiving end.

BEST MODE FOR CARRYING OUT THE INVENTION

Figure 1:
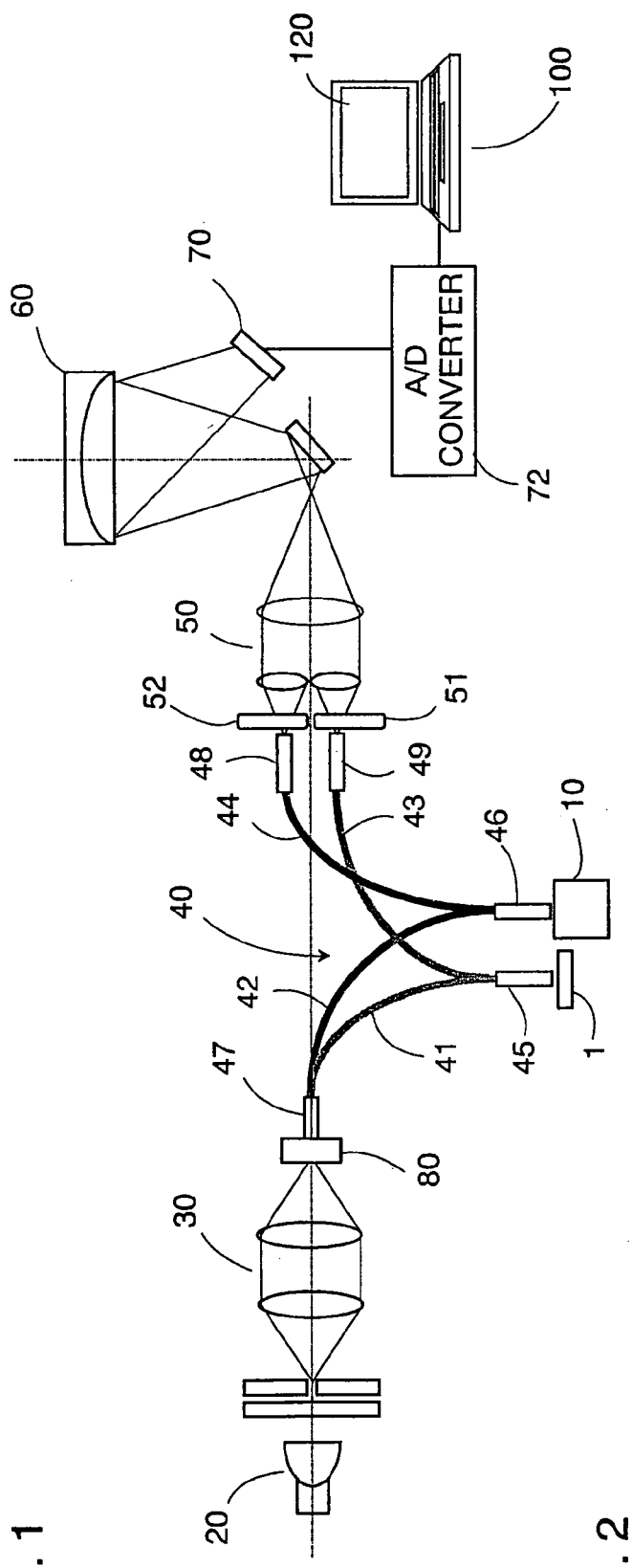
FIG. 1 is a schematic view of a device for calculating a biological component density in accordance with one embodiment of the invention.
Figure 2:
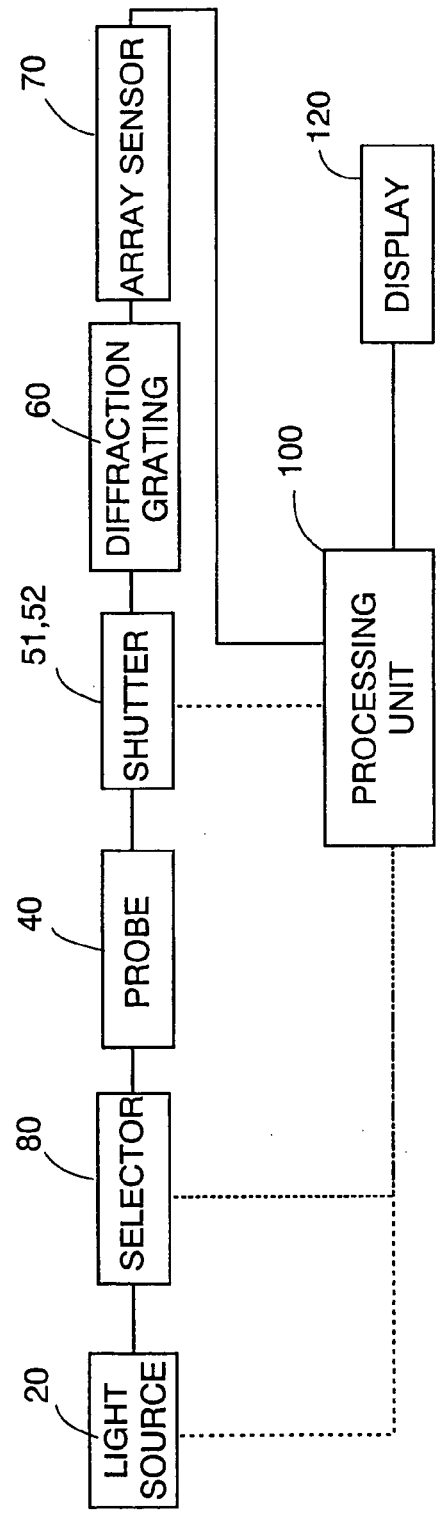
FIG. 2 is a block diagram showing the device of FIG. 1.

FIG. 1 and FIG. 2 show a device for calculating a biological component density in accordance with a first embodiment of the present invention. This device comprises a light source 20 which is a halogen lamp, a light projecting lens group 30 which condenses a light having a NIR spectrum from the light source 20, a probe 40 for irradiating the light which passed the light projecting lens group 30 to a standard board 1 and to a skin 10 of a subject and for receiving the light reflected diffusely therefrom, a condenser lens group 50 which condenses the light from the probe 40, a diffraction grating 60 for dispersing the NIR spectrum which passed the condenser lens group 50, an array sensor 70 for detecting the NIR spectrum dispersed by the diffraction grating 60, and a processing unit 100 which processes the electrical signal indicative of the NIR spectrum from the array sensor 70 thereby calculating the biological component density. In this embodiment, glucose density is calculated as an example of the biological component density by the device. As the array sensor 70, An InGaAs array type photo detector is used. As the processing unit 100, a personal computer is used.

The prove 40 comprises a reference probe and a measurement probe which are made respectively by optical fibers. Each probe comprises a incident guide 41 or 42 which directs the light from the light source 20 to the standard board 1 or the skin 10 of the subject and a reflective guide 43 or 44 which directs the reflected light from the standard board 1 or the skin 10 to the diffraction grating 60. One end of each incident guide and one end of each reflective guide are built in object heads 45 or 46, which are placed opposite the standard board 1 made of ceramic or the skin 10 of the subject, respectively. Both probes are integrated into a light receiving head 47 at each end which receives the light from the light source 20, and the light receiving head 47 is connected to the light projecting lens group 30. Each probe is connected to an output head 48 or 49 at each end which outputs the light to the diffraction grating 60, and each of the output heads is connected to the condenser lens group 50, respectively, through a shutter 51 or 52.

Hereinafter, a measurement principle of the glucose density using the above device will be described briefly. First, the object head 45 is held in proximity to the standard board 1, and the shutter 51 is opened, and the array sensor 70 receives the reflected light (reference signal) from the standard board 1. Then, the object head 46 is brought into contact with the surface of the skin 10 of the subject with a contact pressure of 9.8-49 kPa (100-500 gf/cm$^2$), preferably a fixed pressure of 29.4 kPa (300 gf/cm$^2$), and the shutter 52 is opened, and the array sensor 70 receives the NIR spectrum (biological signal) reflected diffusely within the skin structure through the reflective guide 44. The processing unit 100 processes the obtained reference signal and the obtained biological signal thereby calculating the glucose density of the subject.

In order to determine the glucose density, a suitable calibrating equation is selected from two or more calibrating equations prepared beforehand, and is used. Each of the calibrating equations is different from each other according to the skin thickness of the subject and is prepared for each of plural groups in which skin thickness of the subject are different from each other. Each of the calibrating equations is calculated by a spectral analysis method by multivariate analysis, in which glucose density of which quantity is determined by a normal process is used as a response variable and body tissue spectrum obtained by this spectral analysis device is used as an explanatory variable. As the multivariate analysis, a multiple regression analysis, PLS regression analysis, a neural network, etc. can be applied.

Figure 3:
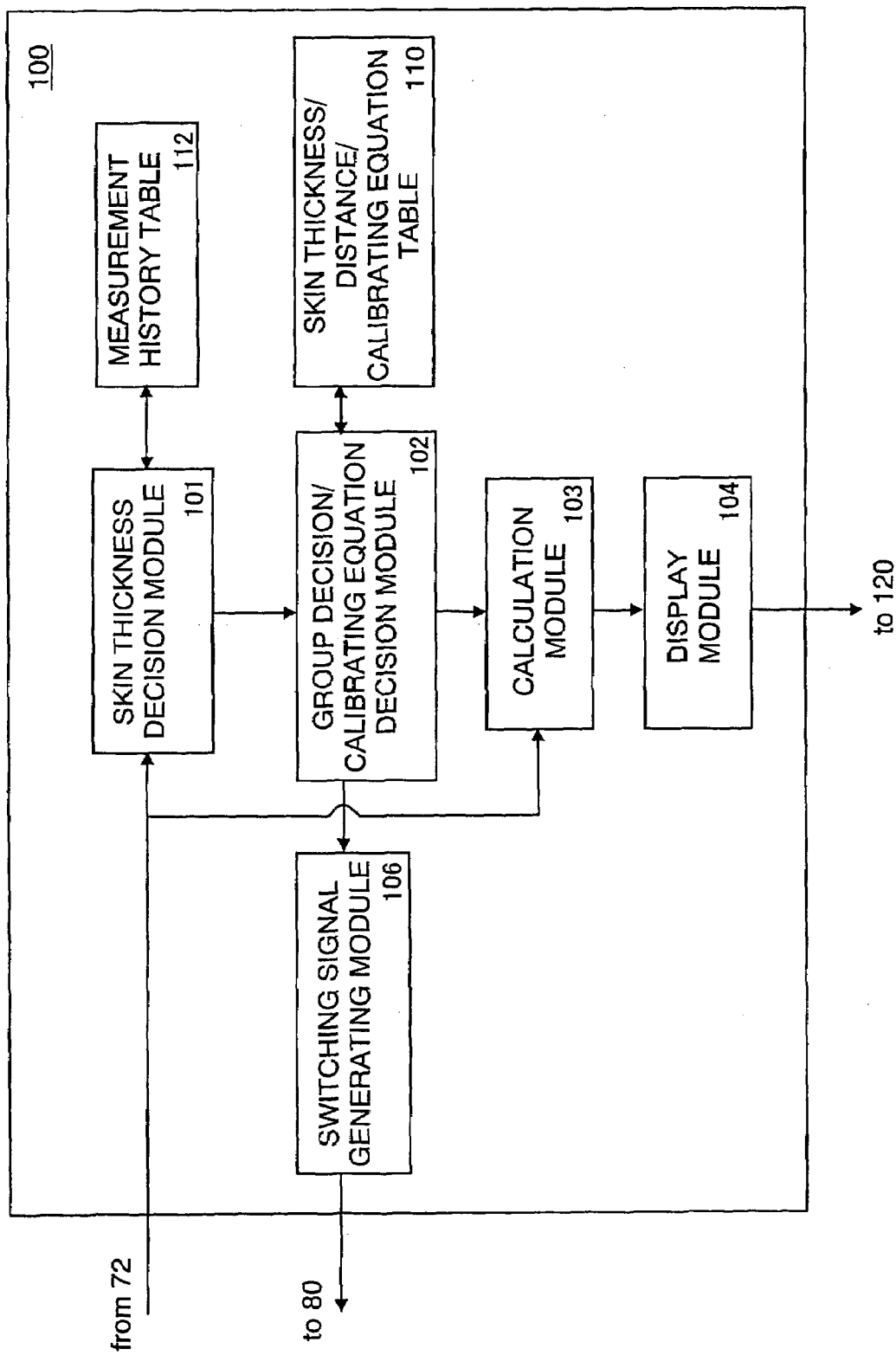
FIG. 3 is a block diagram showing a substantial part of the device of FIG. 2.

FIG. 3 shows various kinds of function modules realized by a program performed in the above processing unit 100 and a table which stores data required for the modules in a memory. This table 110 constitutes a skin thickness memory storing a plurality of the calibrating equations (calibrating equation 1 and calibrating equation 2 in this embodiment) which are each specific to each of the plural groups (group A and group B in this embodiment) classified in terms of a skin thickness parameter indicative of the skin thickness with respect to individuals of a species to which the subject belongs. As the function modules, a skin thickness decision module 101, a group decision module 102, a calculation module 103, and a display module 104 are prepared. The skin thickness decision module 101 receives digital data which was converted by A/D converter 72 from the NIR spectrum outputted from the array sensor 70, and decides the skin thickness therefrom. The group decision module 102 identifies the group from the decided skin thickness and selects the calibrating equation in match with this identified group. The calculation module 103 substitutes the NIR spectrum data into the selected calibrating equation and calculates the glucose density. The display module 104 displays the calculated glucose density on a display 120.

Figure 5:
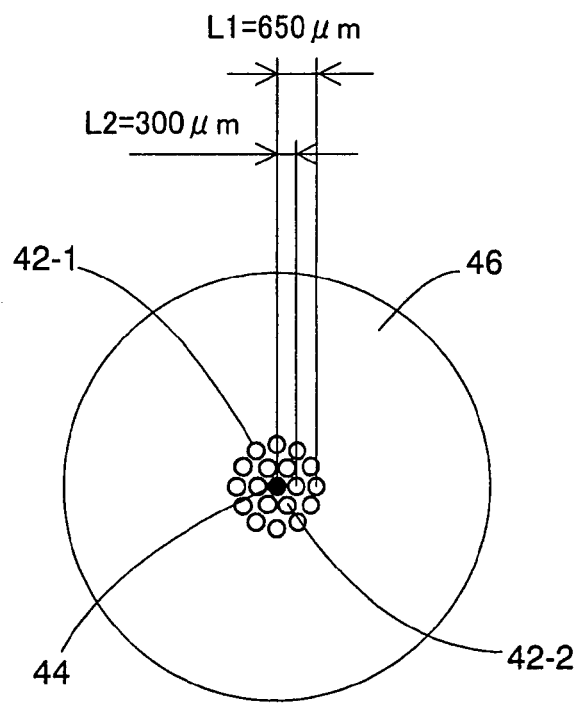
FIG. 5 is a view showing a end face of the probe used for the device.

As shown in FIG. 5, the probe used in this embodiment is designed so that the incident guides 42 irradiating the light from the light source to the skin will be arranged coaxially around the reflective guide 44 which takes out the reflected light from the skin to the array sensor side, on an end face of the object heads 46. As the incident guides, two kinds of guides, which have different distances from the reflective guide, are used. One kind is first incident guides 42-1 spaced by a distance L of 650 μm from the reflective guide, and the other kind is second incident guides 42-2 spaced by a distance L of 300 μm from the reflective guide. There are twelve first incident guides 42-1 and sixth second incident guides. The first and second incident guides are alternatively selected according to the determined skin thickness for the reason which will be stated later. In the table 110 shown in FIG. 3, an instruction for deciding which incident guide to select according to the skin thickness, namely, according to the selected group, is stored, and the above module 102 selects the incident guide according to the group selected from the skin thickness determined first based on the reflected spectrum from the skin. And the module 102 issues an instruction to a switching signal generating module 106, and a switching signal from the module 106 operates a selector 80 to select either the first incident guide or the second incident guide. And then, the glucose density is calculated using the NIR spectrum irradiated from the selected incident guide.

Figure 6:
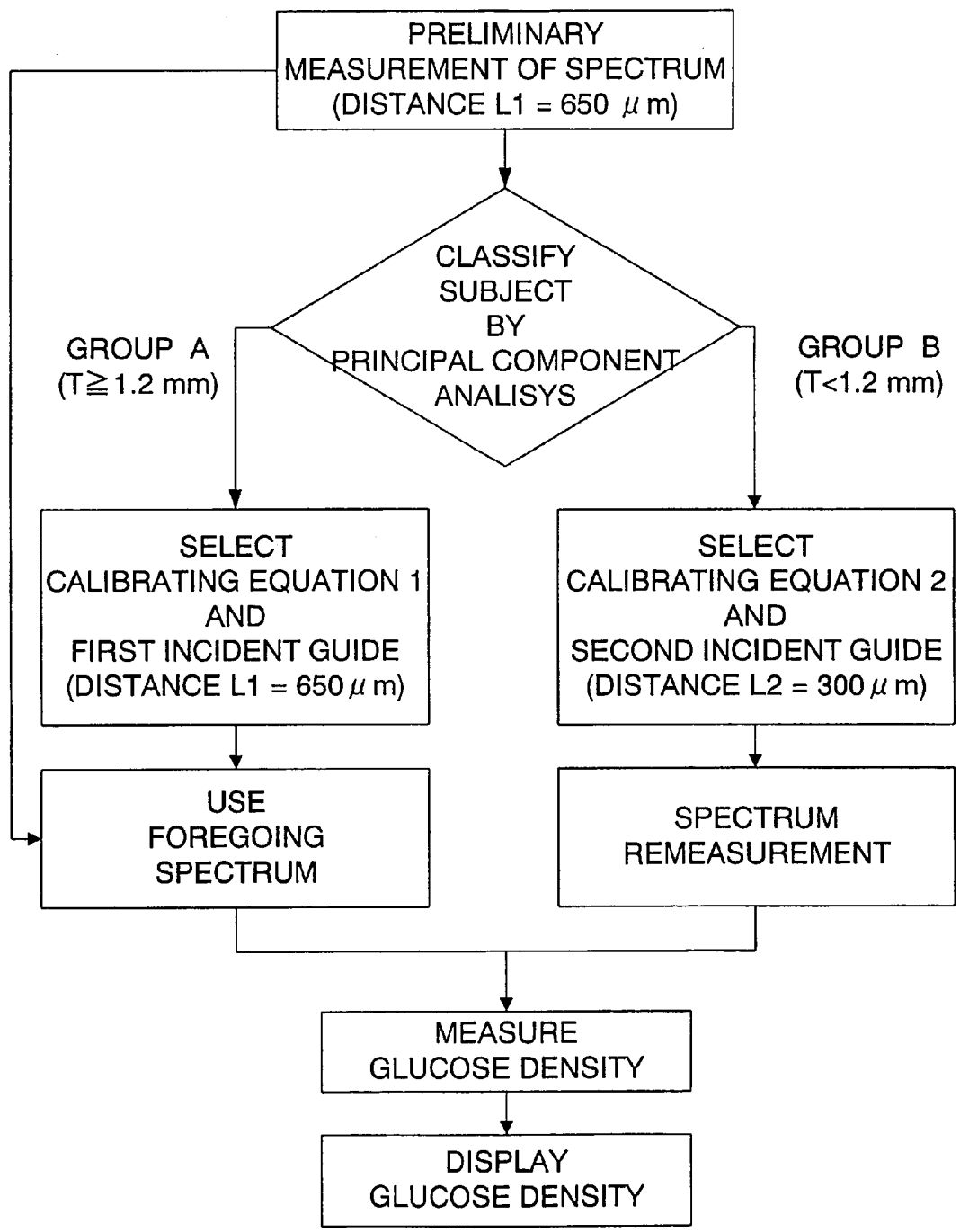
FIG. 6 is a flow chart showing a measurement procedure of the biological component density using the above device.

FIG. 6 is a flow chart showing the measurement procedure of the glucose density in this embodiment briefly. At first, the NIR spectrum reflected from the skin of the subject is preliminarily measured under a measurement condition where the first incident guide is used and the distance L is therefore 650 μm. Then, the skin thickness is determined by a principal component analysis, and the group corresponding to the skin thickness is determined, and the calibrating equation in match with the determined group is selected. When the group A in which the skin thickness is 1.2 mm or more is selected, the glucose density is calculated using the already obtained NIR spectrum. When the group B in which the skin thickness is less than 1.2 mm is selected, the reflected spectrum is measured again using the second incident guide 44-2, and the glucose density is calculated base on the spectrum. This reason will be explained later.

Figure 4:
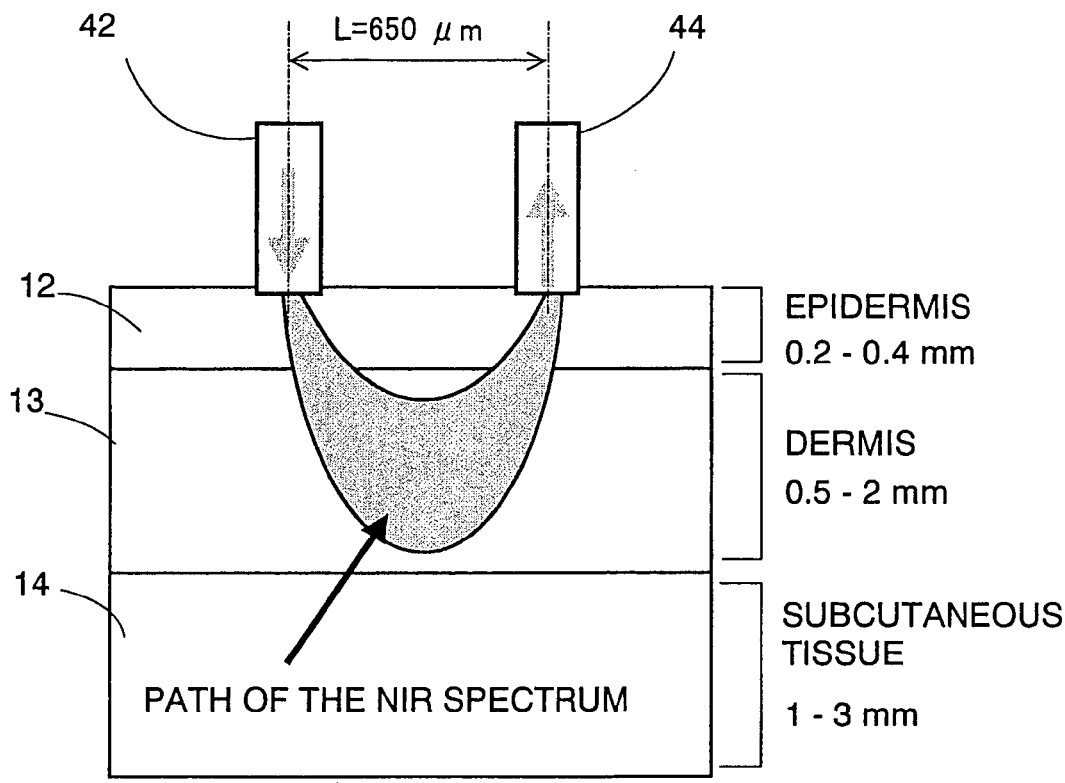
FIG. 4 is a schematic view showing basic principle of the measurement of the biological component density using the above device.

Although the distance L between the incident guide 42 and the reflective guide 44 on the object head 46 can be selected from values other than the above, it is desired that the distance is selected from the range of 0.2 mm-2 mm. The skin structure of living things, including human beings, consists of three layers, the epidermis 12 including the stratum corneum, the dermis 13, the subcutaneous tissue 14, as shown in FIG. 4. The thickness of the epidermis 12 is about 0.2-0.4 mm, the thickness of the dermis 13 is about 0.5-2 mm, and the thickness of the subcutaneous tissue 14 is about 1-3 mm. It is though that the glucose density in the dermis (dermal organization) 13 will follow the glucose density in blood and will change therewith, because blood capillaries, etc. are developed in the dermis 13 and mass transfer according to the blood glucose will occur promptly. In the subcutaneous tissue 14, fat tissue forms the backbone, and glucose, which is water soluble, can not exist evenly in the subcutaneous tissue layer (subcutaneous tissue) 14 easily. Therefore, in order to measure the glucose density in blood with high precision, it is necessary to measure the NIR spectrum of the dermis 13 selectively. In order to catch the NIR spectrum which passed the dermis 13 and reflected diffusely, the distance L between the end of the incident guide 42 and the end of the reflective guide 44 is set to 0.2 mm-2 mm. That is, as shown in FIG. 4, used is a property that the NIR spectrum irradiated from the end of the incident guide 42 penetrates the inside of the skin structure and diffuses, and the backscattering light reaches the reflective guide 44 of the object head. This NIR spectrum takes a U-shaped route shown in FIG. 4, and the depth of the path in the skin structure changes with the distance L. By setting the distance L to the range of 0.2 mm-2 mm, It becomes possible to measure selectively the NIR spectrum reflecting the dermis 13 of the skin structure.

Figure 7:
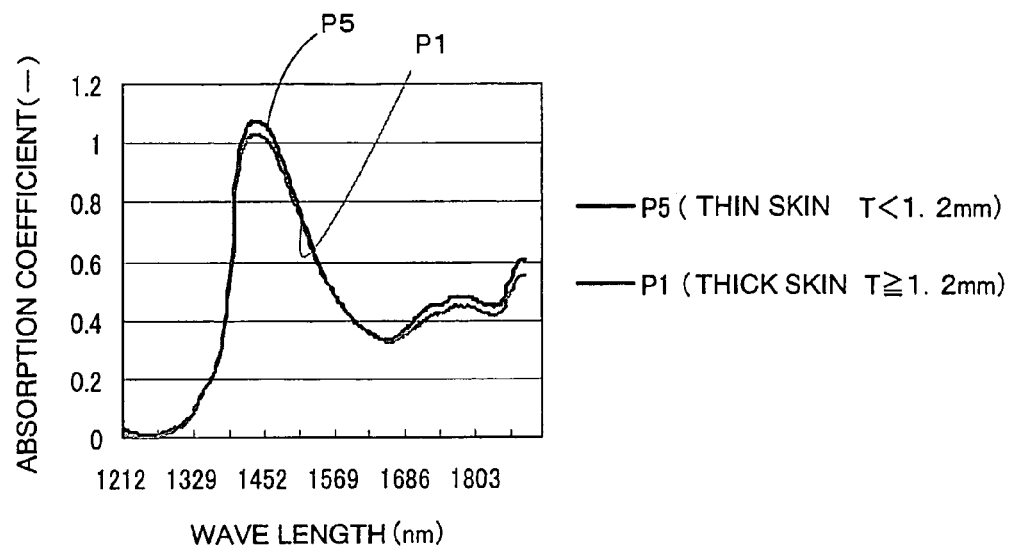
FIG. 7 is a graph showing NIR spectrum measured on skin of a medial side of a forearm of a subject using the device.
Figure 8:
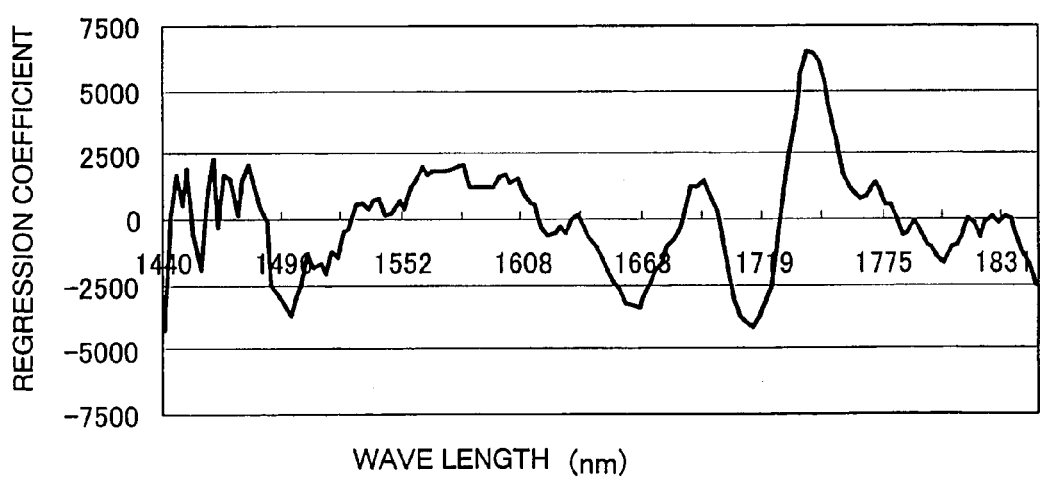
FIG. 8 is a graph showing a relation between a wavelength of NIR spectrum and a regression coefficient for preparing a calibrating equation used for the device based on a statistics procedure.

Next, the preparation of the calibrating equation will be explained. FIG. 7 is a graph showing the NIR spectrum measured by the above device about subjects (P1, P5), and FIG. 8 is a graph showing the regression coefficient for determining the calibrating equation. In the graph shown in FIG. 8, an experiment which fluctuates the glucose density artificially by giving a glucose load via an oral route to one subject was done six times, and one calibrating equation was calculated by multivariate analysis using the NIR spectrum of the skin obtained in the experiment and the data of glucose density measured from blood. As the multivariate analysis, PLS regression analysis was used in this case. The subject was a man, who was 41 years old and healthy. The measurement of the NIR spectrum was done on the skin of the medial side of the left forearm of the subject, and the skin thickness of the measured portion was about 1.5 mm in the sum of the thickness of the epidermis 12 and the dermis 13. The measurement of the skin thickness was done by using the CORTEX (Denmark) ultrasonic fault measuring device "DermaScan C Ver. 3".

The calibrating equation for determining the glucose density will be expressed by the following formula.

$$\text{Glucose density} = \Sigma a_i \cdot x_i + b$$
$$= a_1 \cdot x_1 + a_2 \cdot x_2 + \ldots + a_n \cdot x_n + b$$

an: Regression coefficient at wave length n,
xn: Absorption coefficient at wave length n, and
b: Constant Since the wave length important for the decision of the glucose density has a large regression coefficient, the wave length important for determining the quantity of the glucose density can be presumed by the regression coefficient.

Figure 9:
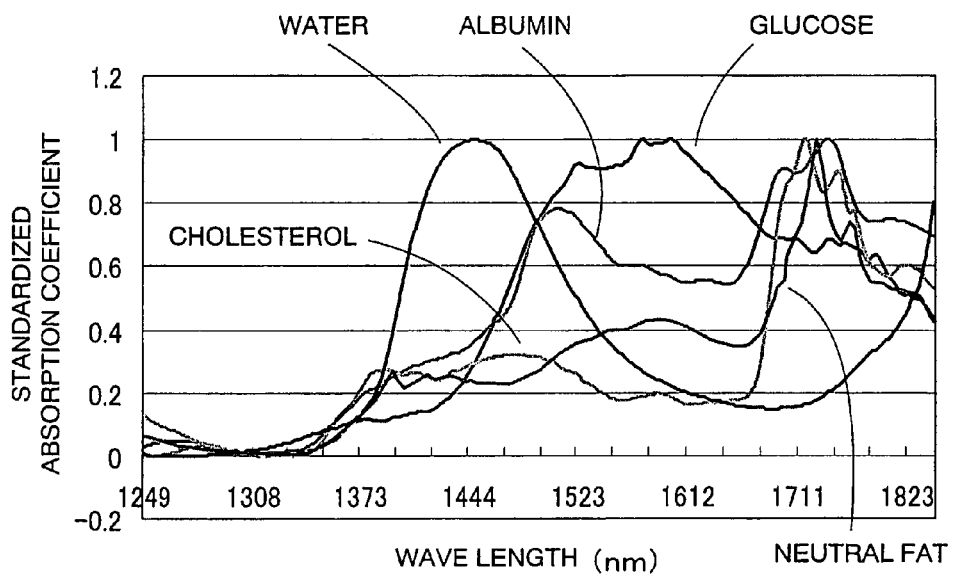
FIG. 9 is a graph showing absorption spectrums of typical biological components.

By the way, it is known that a glucose molecule shows unique absorption at wave length of near 1600 nm as compared with other biological component, as shown in the absorption spectrum of the biological component of FIG. 9. Therefore, it is proved that the regression coefficient which has a characteristic peak at wave length of near 1600 nm in the graph of FIG. 8 reflects the glucose density in the body tissue. In FIG. 9, the maximum absorption coefficient of various kinds of biological components are standardized to 1.

The prove 40 used in order to determine the above calibrating equation has twelve incident guides 42 disposed around the reflective guide 44 at the same distance L (=650 μm), and the calibrating equation corresponding to the subject who belongs to the group in which the skin thickness is 1.5 mm is determined by measuring the subject whose skin thickness is 1.5 mm in the total of the epidermis 12 and the dermis 13 using the prove 40.

Even if a calibrating equation prepared for a certain individual is suitable for that individual, the calibrating equation can not necessarily be applied to other individuals as it is, because there are individual differences in the skin thickness. However, even if there are individual differences, it is expected that a calibrating equation which is generalized to some extent can be prepared by preparing a calibrating equation catching changes of the biological component (glucose), because the biological component aiming at determining the quantity (in this case, glucose) is common irrespective of the individual.

Figure 10:
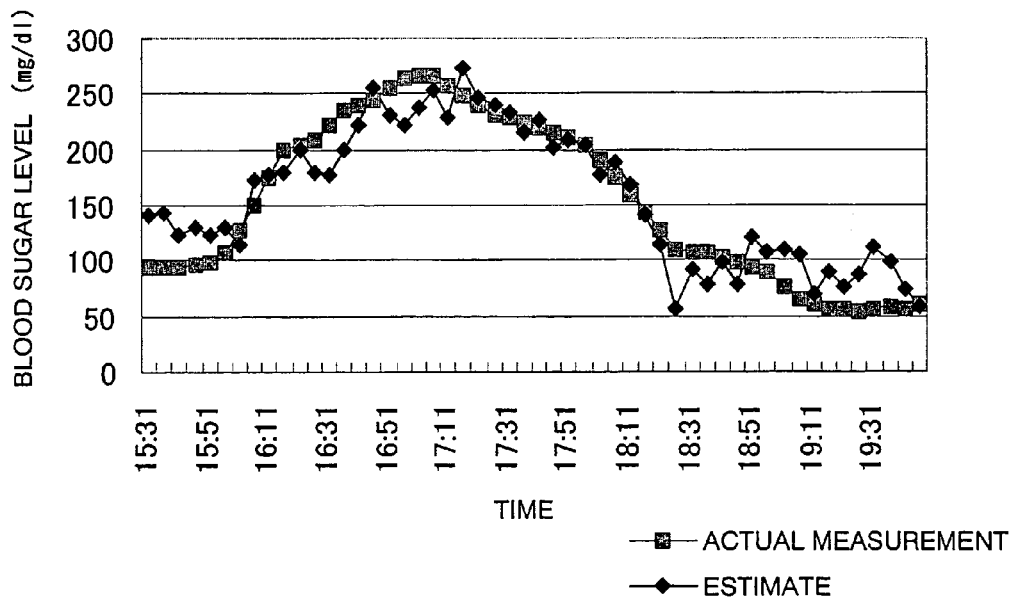
FIG. 10 is a graph showing a relation between an estimate and an actual measurement when glucose density which changes as time go on was measured using the device.
Figure 11B:
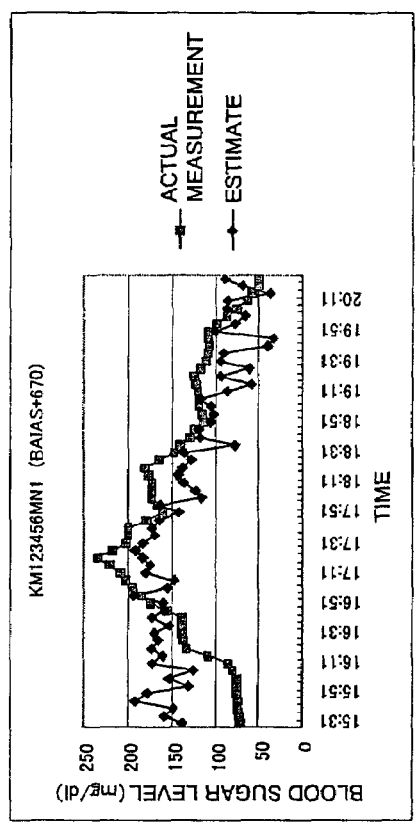
FIGS. 11A-11D are graphs showing a relation between an estimate and an actual measurement of the glucose density, respectively, when subjects whose skin thickness are different from each other were measured by one calibrating equation using the above device.
Figure 11D:
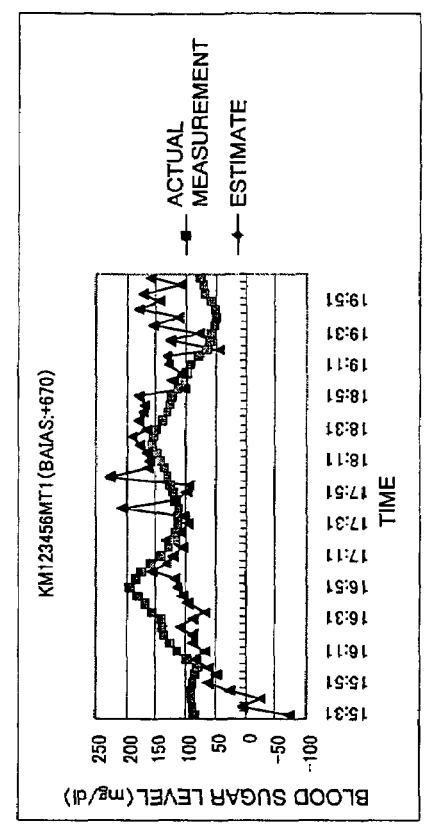
Figure 11A:
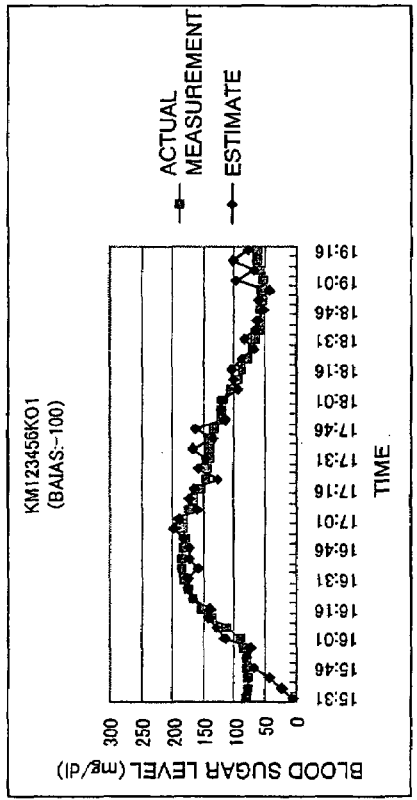
Figure 11C:
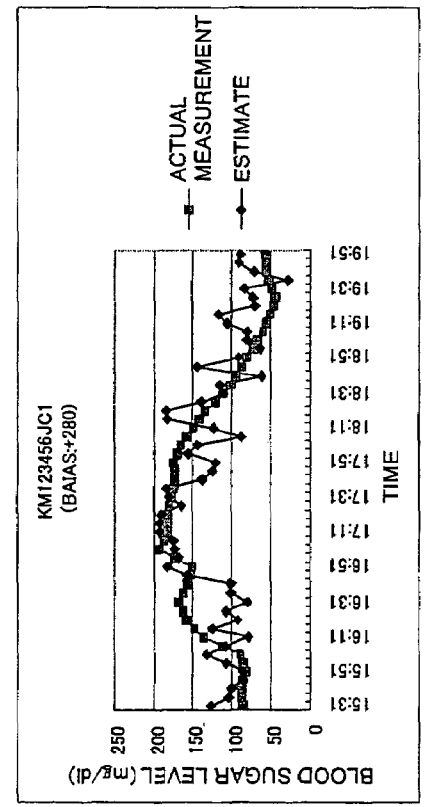

Next, shown in FIGS. 10 and 11 are results (estimates) of changes of glucose density which were estimated to five subjects P1-P5 including the subject P1, using the calibrating equation which was prepared, as stated above, for the subject P1, and actual changes (actual measurements) of glucose density measured from blood, respectively. The attribute of these five subjects are shown in Table 1.

TABLE 1

|  |  | Sex | Age | Health condition | Skin thickness (mm) |
|---|---|---|---|---|---|
| Subject | P1 | man | 41 | good | 1.3-1.5 |
|  | P2 | man | 37 | good | 1.2-1.4 |
|  | P3 | man | 47 | good | 0.9-1.0 |
|  | P4 | man | 27 | good | 1.0-1.1 |
|  | P5 | man | 35 | good | 0.8-0.9 |

It became clear from the graph of FIG. 10 that when the change of the glucose density of the subject P1 was estimated by the calibrating equation prepared from the data of the subject P1, a good estimation in which the correlation coefficient between actual measurement and the estimate is about 0.9 is possible.

Figure 12:
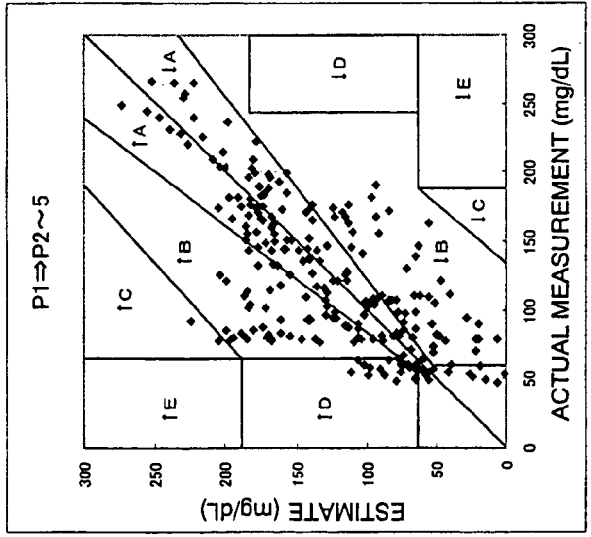
FIG. 12 is a graph showing a correlation between an estimate and an actual measurement of the glucose density, when subjects whose skin thickness are different from each other were measured by one calibrating equation using the above device.

Moreover, it became clear from the FIG. 11 that when the change of the blood sugar level of other subjects (P2-P5) were estimated by the calibrating equation prepared for the subject P1, a good estimation is possible to the subject P2 but is difficult to other subjects P3-P5. The graph of FIG. 12 shows a relation between the actual measurements and the estimates in the above case where the change of the blood sugar level of five subjects (P1-P5) were estimated by one calibrating equation prepared for the subject P1. In this case, the correlation coefficient is 0.69, so it is understood that the correlation coefficient becomes low when the calibrating equation peculiar to one subject (P1) is applied to the measurements of glucose density of other four persons.

Next, calibrating equations were prepared to each subject P2-P5, respectively, based on data of actual glucose density which were measured from blood after the glucose load experiment done six times to each of the subjects P2-P5, respectively. More particularly, the glucose load experiments were done six times to each subject, and six calibrating equations (CE1-CE6) were prepared from data of six kinds of combinations (C1-C6) including five experiments out of six experiments. And, using each of the calibrating equations, the glucose density of the remaining experiment out of the combination was estimated, and the correlation between the actual measurement and the estimate was examined. And, as shown in Table 2, by substituting the NIR spectrum data obtained from the glucose load experiment done for every subject into the six calibrating equations prepared for each of the subjects, the glucose density of all the subjects were measured (estimated) mutually, and thereby the reliability of the estimates were examined.

TABLE 2

|  |  |  | Subjects |  |  |  |  |
| --- | --- | --- | --- | --- | --- | --- | --- |
|  |  |  | P1 | P2 | P3 | P4 | P5 |
| Group A | Calibrating | P1 | ○ | ○ | x | Δ | x |
| (T ≧ 1.2 mm) | equations | P2 | ○ | ○ | ○ | x | x |
| Group B |  | P3 | x | Δ | ○ | ○ | ○ |
| (T < 1.2 mm) |  | P4 | x | x | ○ | ○ | ○ |
|  |  | P5 | x | x | x | x | x |

In this Table 2, if the average of the correlation coefficients between the six estimates which were calculated about each of the subjects and corresponding actual measurements is 0.7 or more, a "○" mark is inscribed, and if the average is 0.6 or more and less than 0.7, a "Δ" mark is inscribed, and if the average is less than 0.6, a "x" mark is inscribed. As understood from Table 2, in this experiment in which five subjects were used, these subjects are roughly divided into two attributes (Group A, Group B), and, in each group, the glucose density can be estimated (measured) accurately with each other by the calibrating equation prepared mutually. These groups A and B are classified according to the skin thickness, as is clear from Table 1. Each of the skin thickness in Table 1 was calculated by the average of the skin thickness (the sum of the epidermis and the dermis) of three places chosen arbitrarily from a ultrasound tomogram.

It is turned out from Table 2 that the calibrating equation peculiar to the subject P5 is not effective in measurement of its own glucose density, and the calibrating equations peculiar to the subject P3 and P4 who belong to the same group B are effective in measurement of the glucose density of the subject P5. This is attributed to the fact that the skin thickness of the subject P5 is quite thin. Summarizing the above, the group classified according to the skin thickness is divided into the group A in which the skin thickness is 1.2 or more and the group B in which the skin thickness is less than 1.2 and, as for the group B in which the skin thickness is thin, the calibrating equations prepared for the subjects whose skin thickness are 0.9 mm-1.1 mm are effective.

As is clear from the above experiment result, the glucose density can be measured accurately without complicated processes of preparing calibrating equations for each subject, if a patient or a subject, who is a measuring object of the biological component, is classified according to the skin thickness and the calibrating equations are prepared for each of the classified groups, not for each individual, beforehand.

As the calibrating equation, two kinds of calibrating equations are prepared beforehand and are stored in the table 110 in the processing unit 100. One is a calibrating equation 1, which estimates the glucose density of subjects whose skin thickness, the sum of the epidermis and the dermis, are 1.2 mm or more, and the other is a calibrating equation 2, which estimates the glucose density of subjects whose skin thickness are less than 1.2 mm.

The calibrating equation 1 is expressed as follows;

$$\text{Glucose density (mg/dl)} = a_{1420} \cdot x_{1420} + a_{1423} \cdot x_{1423} + \cdots + a_{1837} \cdot x_{1837} + a_{1840} \cdot x_{1840} + b$$

$a_n$: Regression coefficient at wave length n,
$x_n$: Absorption coefficient at wave length n, and
b: Constant The calibrating equation 2 is expressed as follows;

$$\text{Glucose density (mg/dl)} = c_{1420} \cdot x_{1420} + c_{1423} \cdot x_{1423} + \cdots + c_{1837} \cdot x_{1837} + c_{1840} \cdot x_{1840} + d$$

Figure 14:
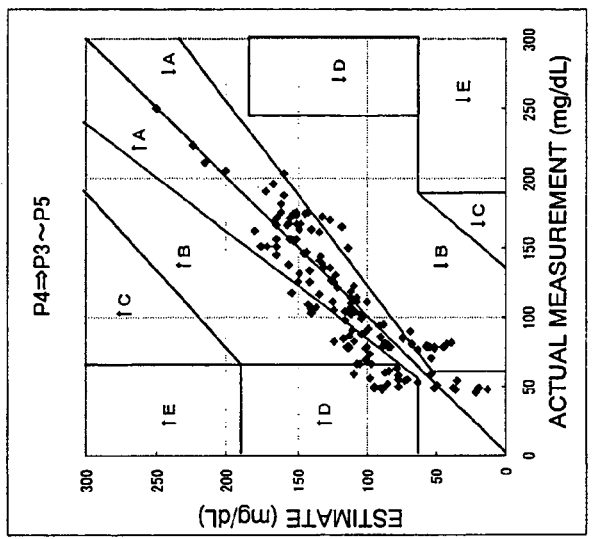
FIG. 14 is a graph showing a correlation between an estimate and an actual measurement of the glucose density, when subjects who belong to other group with the same skin thickness are measured by one calibrating equation in match with the group using the device.
Figure 13:
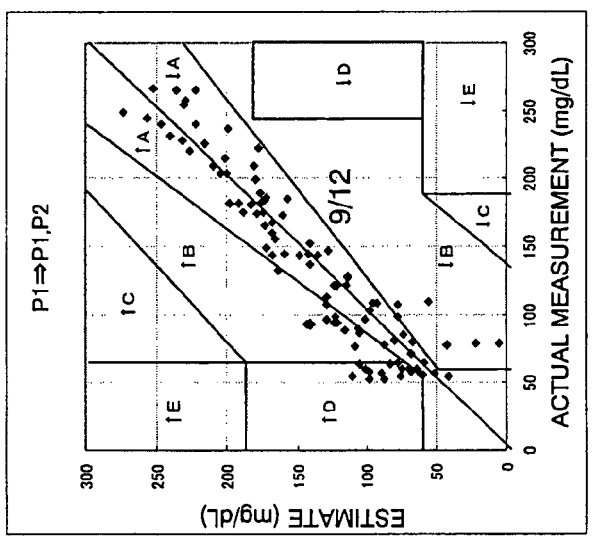
FIG. 13 is a graph showing a correlation between an estimate and an actual measurement of the glucose density, when subjects who belong to one group with the same skin thickness are measured by one calibrating equation in match with the group using the device.

$c_n°$: Regression coefficient at wave length n,
$x_n$: Absorption coefficient at wave length n, and
d: Constant In this way, by selecting the calibrating equation according to the groups classified in terms of the skin thickness, the reliable measurements in which the correlation coefficient between the actual measurement and the estimate is high, for example, 0.93 or 0.85 as shown in FIGS. 13 and 14, became possible.

Moreover, in this embodiment, since the first incident guide 42-1 and the second incident guide 42-2 are switched according to the skin thickness of the subject in order to change the distance L between the incident light and the reflected light, the U-shaped optical path shown in FIG. 4 can reach the dermal organization certainly, whereby the reliability of the measurement can be raised. That is, the distance L is made small for the group with thin skin thickness to form the optical path in a shallow area of the skin and to catch the dermis.

Figure 15:
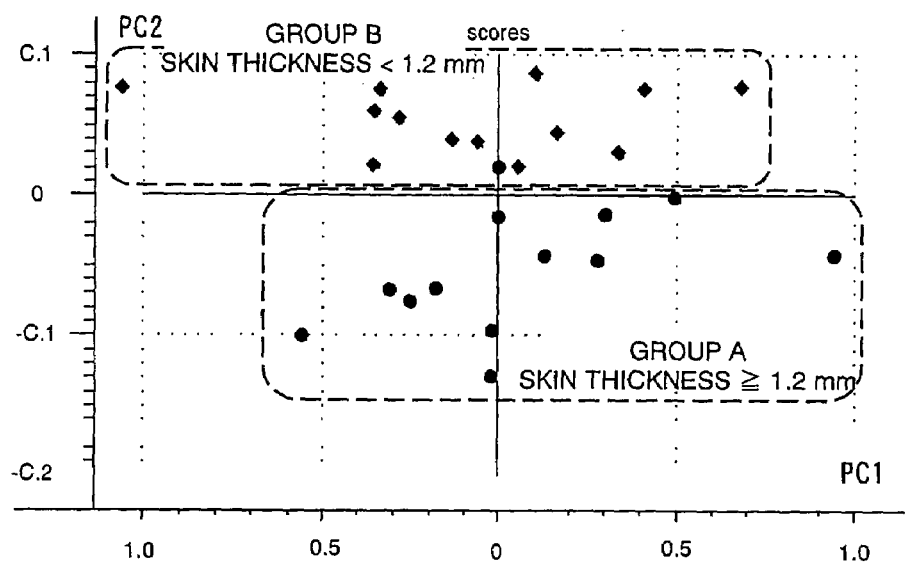
FIG. 15 is a graph showing a result of principal component analysis of the NIR spectrum reflected from a skin.
Figure 16:
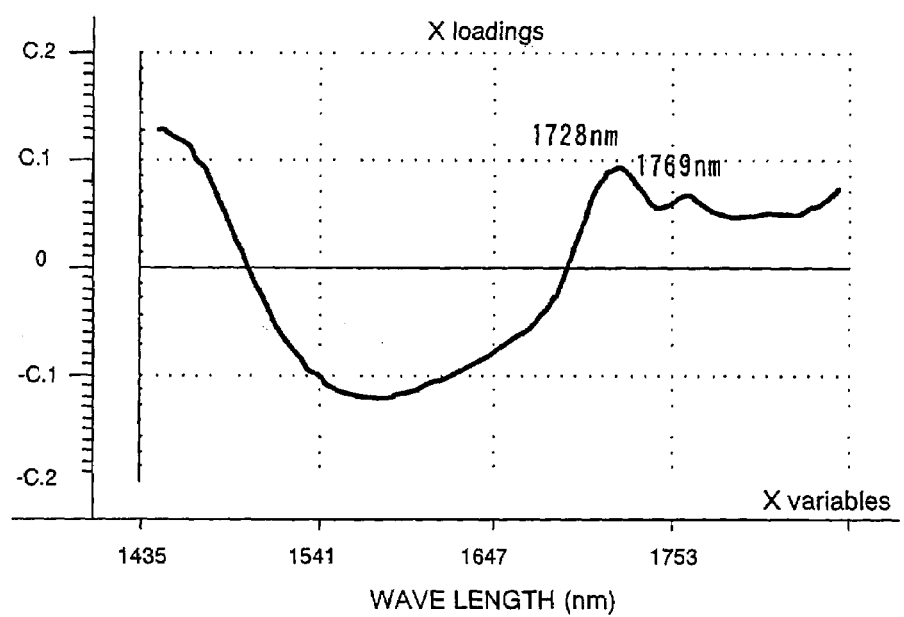
FIG. 16 shows loading plots of a second principal component of the above principal component analysis.

In this embodiment, the data of the NIR spectrum reflected from the skin is effectively used in order to measure the skin thickness, in addition to the measurement of the glucose density. The NIR spectrum outputted from the array sensor 70 is sent to the processing unit 100 as digital data through A/D converter 72, and is analyzed based on a principal component analysis in the skin thickness decision module 101 provided in the processing unit 100, and is classified into the group A in which the skin thickness is 1.2 mm or more and the group B in which the skin thickness is less than 1.2 mm. FIG. 15 shows the result of the classifying of the subjects based on the principal component analysis. As is clear form the FIG. 15, the group A in which the skin thickness, the sum of the epidermis and the dermis, is 1.2 mm or more and the group B in which the skin thickness is less than 1.2 mm are clearly classified by a second principal component (PC2). FIG. 16 shows loading plots of the second principal component, in which there are characteristic peaks at a wavelength of 1728 nm and 1769 nm, and these peaks correspond to the peaks of the neutral fat shown in FIG. 9. Therefore, magnitude of contribution of the second principal component can be interpreted as the reach of the light to the subcutaneous tissue (fat tissue), therefore, the principal component analysis can be used for the classification of the skin thickness as an alternative characteristic of the skin thickness. That is, the individual difference of the skin thickness becomes the difference of the reach of the light to the subcutaneous tissue, and appears as a configuration difference of the NIR spectrum in the end. By classifying the configuration difference of the NIR spectrum using the principal component analysis, the classification of the subject based on skin thickness became possible. Besides the principal component analysis, qualitative analysis such as cluster analysis and discriminant analysis can be used for the classification based on the multivariate analysis. In this way, the measurement of the skin thickness can be attained by software for analyzing the reflected spectrum from the skin, and therefore, it is not necessary to use another hardware to measure the skin thickness. So, the device can be simplified.

The switch between the two kinds incident guides, the first incident guide 42-1 and the second incident guide 42-2, arranged as shown in FIG. 5, is done by the selector 80 provided in the path from the light projecting lens group 30 to the probe 40. That is, the light from the light source 20 is led to the incident guide 42-1 or 42-2 alternatively by the selector 80. This selector 80 includes a light volume regulator and two mechanical shutters. The light volume regulator adjusts the amount of the incident lights to the first incident guide 42-1 and the amount of one to the second incident guide 42-2, at a rate of 2:1. The selector 80 is operated by a signal from the switching signal generating module 106 realized in the processing unit 100 to validate either the first incident guide or the second incident guide. That is, when the distance L1 of 650 µm is selected, the mechanical shutter on a side of the first incident guide 42-1 is opened and the shutter on a side of the second incident guide 42-2 is closed.

The measurement conditions of the glucose density of last time, such as a calculated skin thickness, etc., are stored in a measurement history table 112 in the processing unit 100, and if a subject is fixed to the same people as the last time, the procedure of determining the skin thickness can be skipped after the first measurement by taking out the skin thickness from the measurement history table 112. So, the measurement can be shortened.

Although the above embodiment shows the example in which two groups A and B, two calibrating equations 1 and 2, and two distances L1 and L2 are prepared according to the skin thickness, the present invention is not limited to the above, and it is possible to use three or more groups, and three or more calibrating equations and distances corresponding to the groups.

Figure 17:
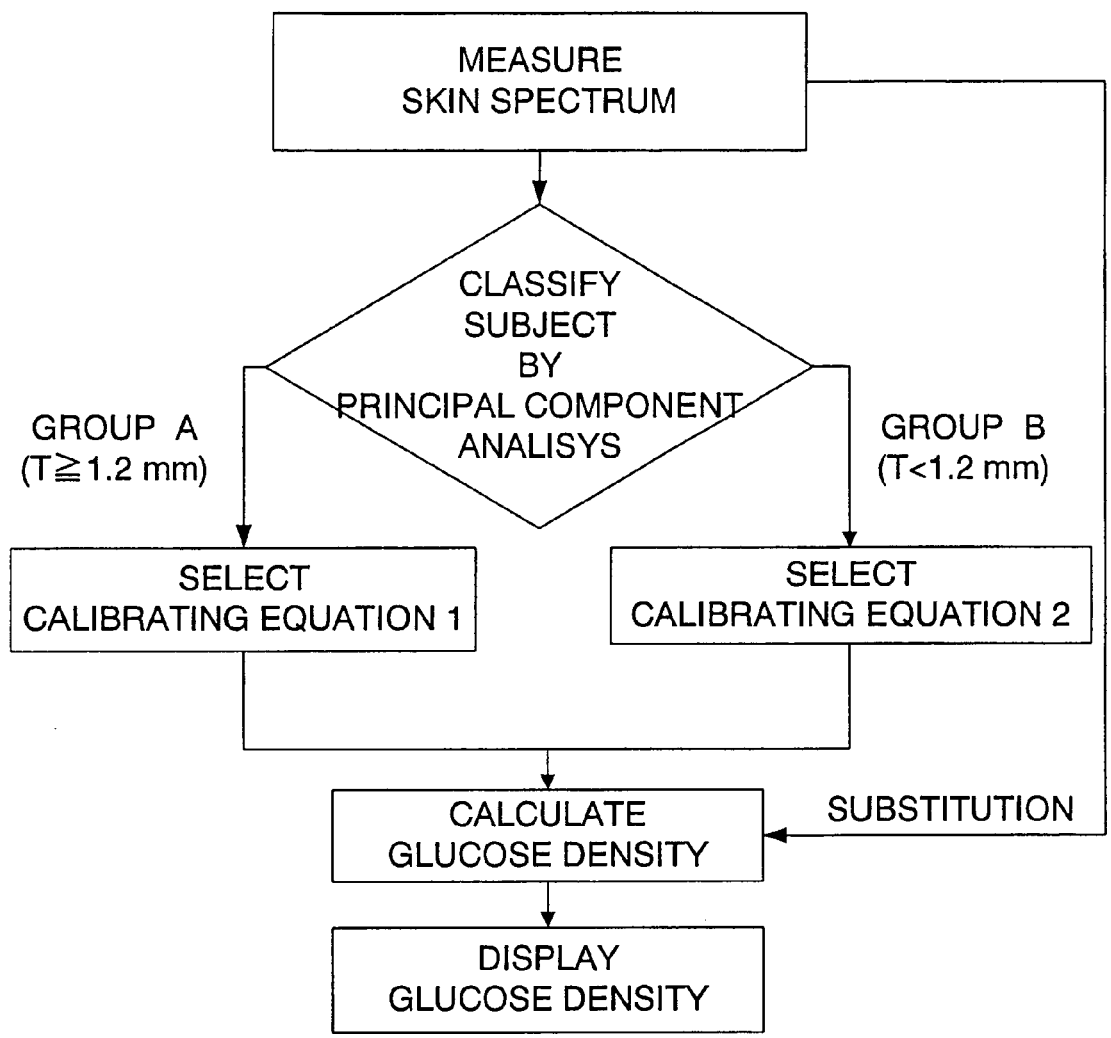
FIG. 17 is a flow chart showing a method for calculating the biological component density in accordance with a second embodiment of the invention.
Figure 18:
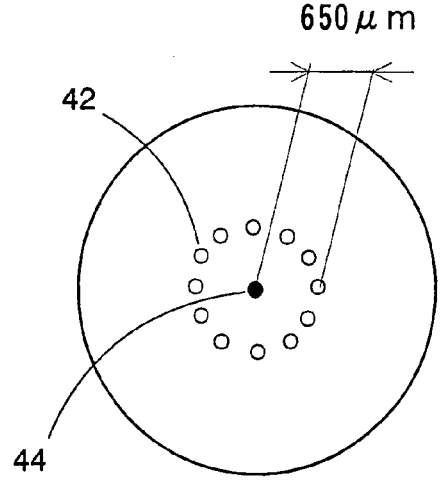
FIG. 18 is a view showing an end face of a probe used for the above method.

The present invention is not limited to the above embodiment, the distance between the incident guide and the reflective guide on the end face of the object head 46 may be fixed to 650 µm, as a second embodiment shown in FIGS. 17 and 18. In this embodiment, reliable measurements of the glucose density is also possible by the same procedure as the above embodiment, i.e., first, the skin thickness of the subject is measured by the principal component analysis of the reflective spectrum from the skin, which is also used for the measurement of the glucose density, and the calibrating equation in match with the group corresponding to the skin thickness is selected.

Figure 19:
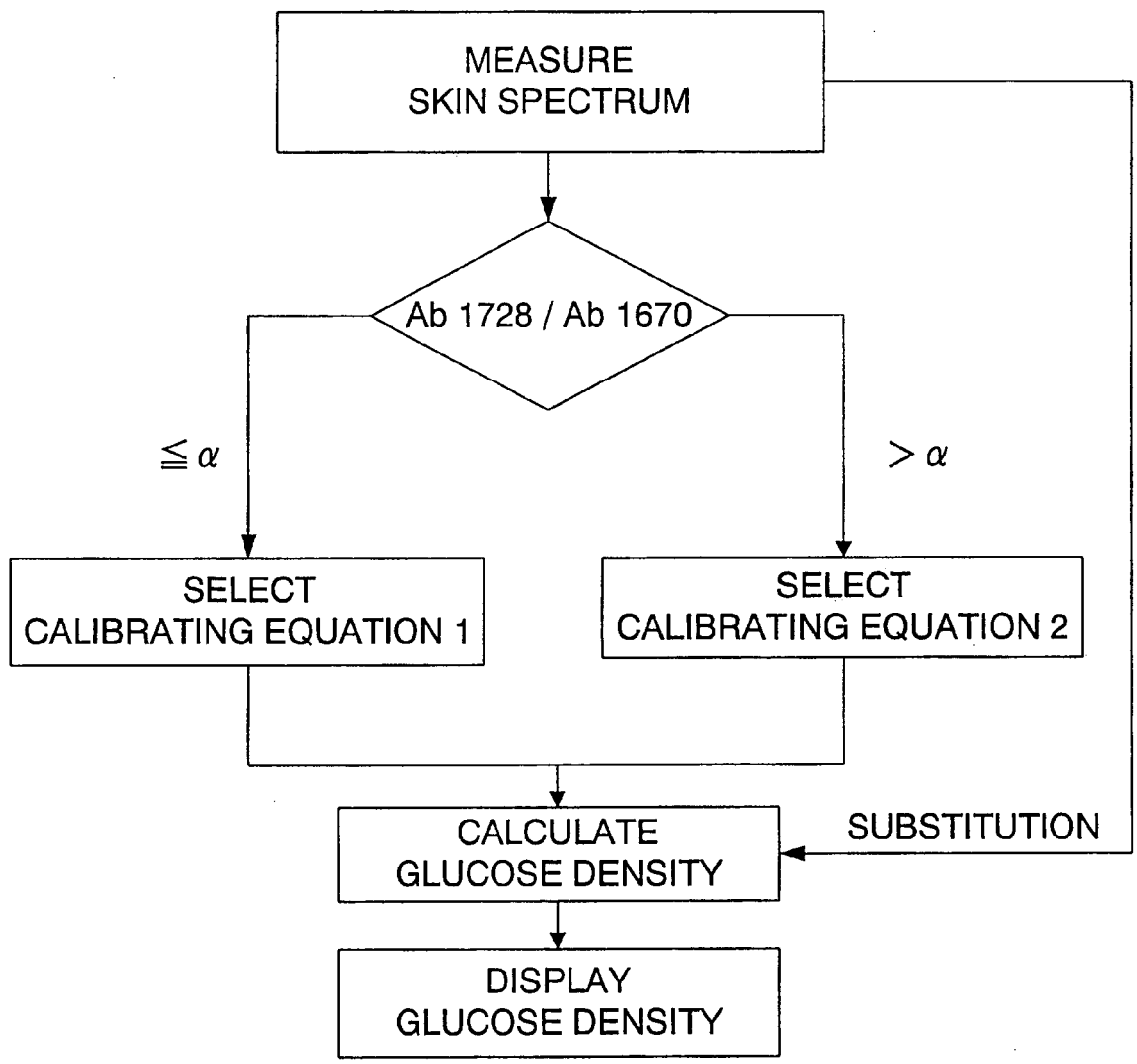
FIG. 19 is a flow chart showing a method for calculating the biological component density in accordance with a third embodiment of the invention.

FIG. 19 shows a third embodiment of the present invention, in which, the skin thickness is determined by using a ratio of an absorption coefficient of the NIR spectrum reflected from the skin of the subject at a wavelength of 1728 µm (Ab1728) to an absorption coefficient at a wavelength of 1670 µm (Ab1670), in order to select the group classified in terms of the skin thickness. That is, when "Ab1728/Ab1670>$\alpha$($\alpha$: constant)", then the skin thickness is judged to be less than 1.2 mm, and when "Ab1728/Ab1670$\leq\alpha$", then the skin thickness is judged to be 1.2 mm or more. After that, like the above embodiment, the glucose density is measured by substituting the NIR spectrum data into the calibrating equation in match with the selected group. In this embodiment, the probe of which distance between the incident guide and the reflective guide is 650 µm is used.

In this way, the group can be selected based on the skin thickness using the unique absorption wave length of the NIR spectrum caused by the fat component, on a ground that the amount of subcutaneous fat is proportional to the skin thickness (reaching depth to the dermis). In this case, too, like the above embodiment, the skin thickness can be calculated by the non-invasive technique without adding another hardware.

Figure 20:
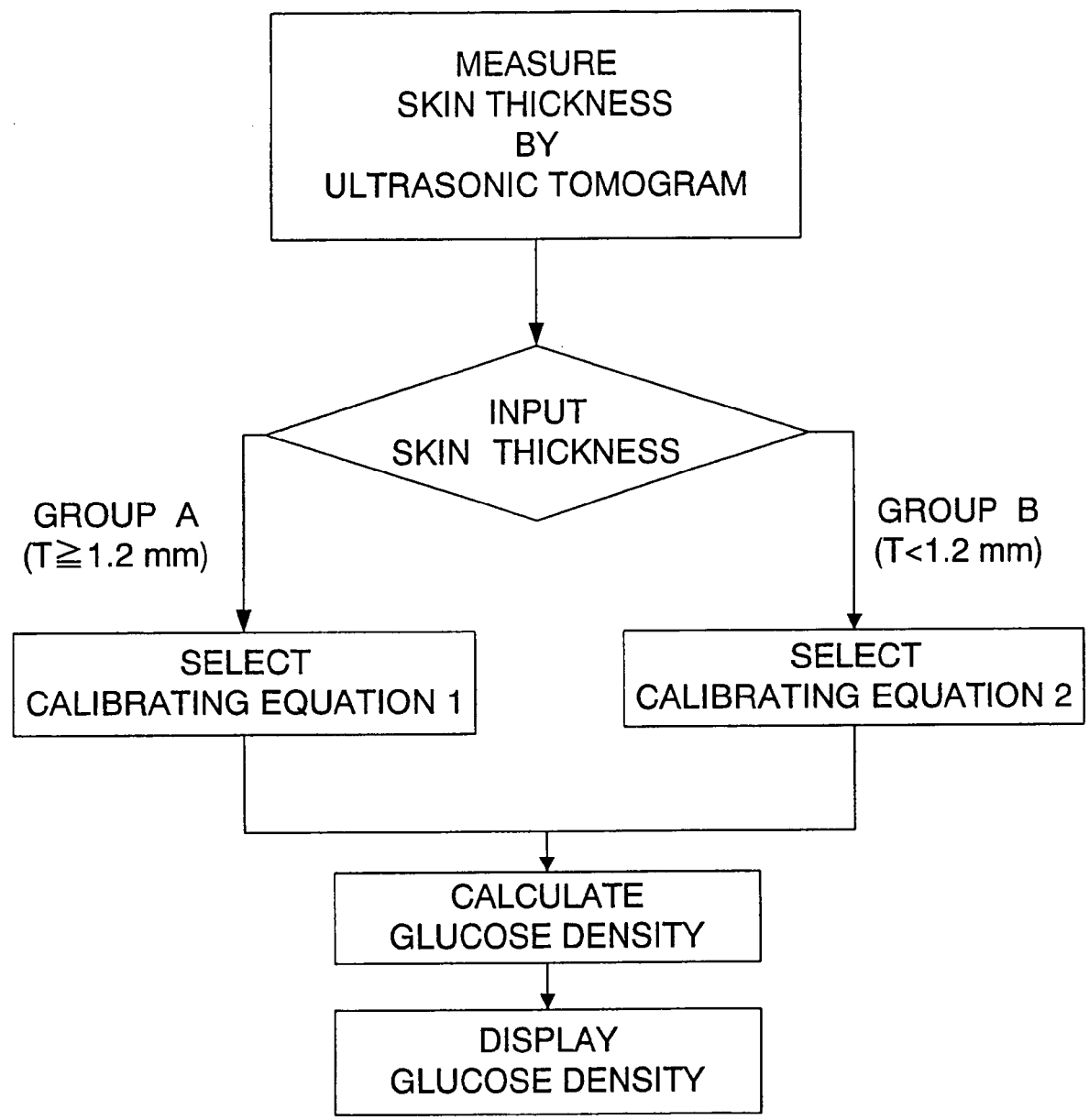
FIG. 20 is a flow chart showing a method for calculating the biological component density in accordance with a fourth embodiment of the invention.

The present invention is not limited only to the above embodiment, it is also possible to use an ultrasonic tomogram device thereby determining the skin thickness of the subject, as a fourth embodiment shown in FIG. 20. The skin thickness can be measured by using the CORTEX (Denmark) ultrasonic fault measuring device "DermaScan C Ver. 3".

Besides the ultrasonic tomogram device as a means of measuring the skin thickness, an ultrasonic measurement method which does not use a tomogram (fault image) may be used. Also, an optical coherence tomography may be used for the measurement of the skin thickness. Typical examples of the optical coherence tomography are a low coherence interferometry and a optical frequency scanning method. Both of the methods can measure a fault of a living body with a resolution of dozens micrometer order. And, the skin thickness can be measured from a tomogram of the skin obtained after irradiating NIR laser light to a medial side of the forearm.

It is also possible to classify the groups in more detail and prepare calibrating equations for each of the groups, based on indexes for classifying the subject's attributes, such as an amount of keratin moisture of a skin, a moisture density of skin structure, a density of skin structure, a color of a skin, a surface roughness of a skin, sex, age, and a race, in addition to the skin thickness. In this case, more precise measurements of the glucose density to a variety of subjects is expected.

Although the glucose was taken as an example of a biological component to be measured in the above embodiments, this invention is not necessarily limited to this and can be used for a quantitative analysis of a biological component such as an amount of organization moisture, neutral fat, cholesterol, HbA1c (saccharification hemoglobin), fructosamine, albumin, globulin, uric acid, etc. Furthermore, this invention can be used for measurements of a degree of skin health, skin age, a degree of aging, and a tension of a skin, etc. which are, respectively, alternative characteristics of the above biological components.

The invention claimed is:

1. A device for calculating a biological component density of a subject, which comprises:
   a light source generating a light having a NIR (near infrared) spectrum;
   an incident guide directing said light to a skin of said subject;
   a reflective guide directing the NIR spectrum reflected back from within said skin;

a sensor receiving said NIR spectrum through said reflective guide to provide NIR data thereof;
a processing unit which substitutes said NIR data into a predetermined calibrating equation to calculate the biological component density of said subject, characterized in that
said device further includes:
a skin thickness memory storing a plurality of the calibrating equations which are different from each other and which are each specific to each of a plural groups classified in terms of a skin thickness parameter indicative of a skin thickness with respect to individuals of a species to which said subject belongs; and
a means for determining the skin thickness parameter with a non-invasive technique to identify the group of the subject in accordance with the determined skin thickness parameter;
said processing unit operating to derive one of said calibrating equations from said skin thickness memory in match with the identified group in order to calculate the biological component density of the subject,
wherein
said skin thickness memory stores two calibrating equations which are different from each other, one corresponding to a group in which the skin thickness is 1.2 mm or more, and the other corresponding to a group in which the skin thickness is less than 1.2 mm, and wherein
said incident guide has a light projecting end adapted to be held in close proximity to said skin, and said reflective guide has a light receiving end adapted to be held in close proximity to said skin,
said light receiving end being spaced from said light projecting end by a distance of 2 mm or less across said skin,
said incident guide and said reflective guide being made respectively by optical fibers which are integrated into a single probe head having an object end to which said light projecting end and said light receiving end are exposed,
said probe including a plurality of different incident guides and a single reflective guide, said different incident guides having individual light projecting ends which are spaced by different distances, respectively from said light receiving end on said object end,
a selector being provided to selectively couple one of said different incident guides to said light source so as to direct said light having the NIR spectrum through the selected incident guide,
said processing unit further including:
a table storing a relation between each one of said groups and each one of said different light incident guides; and
a module which analyzes said NIR data statistically based upon the NIR spectrum irradiated through one of said incident paths and received from said skin to determine said skin thickness parameter and to identify the corresponding one of said group,
said module operating to select from said table one of said different incident guides as corresponding to the identified group,
said module calculating said biological component density based upon said NIR spectrum when the selected incident light guide corresponds with the incident guide which directed the light having the NIR spectrum to the skin to determine the skin thickness parameter,
said module enabling said selector to activate the other incident guide and directing the light having the NIR spectrum to said skin once again through the activated incident guide and calculating said biological component density based upon the NIR spectrum received from the skin when the selected incident guide does not correspond with the incident guide which directed the light having the NIR spectrum to the skin to determine the skin thickness parameter.

2. The device as set forth in claim 1, wherein a plurality of said incident guides having the light projecting ends spaced by the same distance from said light receiving end are arranged about said single reflective guide to have the light projecting ends coaxial with said light receiving end.

3. The device as set forth in claim 1, wherein the biological component density is glucose density.

4. A method of calculating a biological component density of a subject, said method comprising the steps of:
irradiating a light of NIR (near infrared) spectrum to a skin of the subject;
receiving said light of NIR reflected from said skin to obtain NIR spectrum data thereof;
substituting said NIR spectrum data into a predetermined calibrating equation to obtain a biological component density of said subject;
said method further including the step of:
preparing a plurality of the calibrating equations which are different from each other and are each specific to each of a plural groups which are classified in terms of a skin thickness parameter indicative of a skin thickness with respect to individuals of a species to which said subject belongs;
determining said skin thickness parameter of the subject with a non-invasive technique and identifying the group of the subject in accordance with the determined skin thickness parameter, deriving one of said calibrating equations in match with the identified group in order to calculate the biological component density of the subject, wherein
said NIR spectrum is irradiated to said skin selectively through one of a plurality of different incident paths which are spaced by different distances along a skin surface from a common reflective path through which said NIR spectrum is reflected out from the skin, said different incident paths being assigned as being specifically suitable to said groups, respectively,
said NIR spectrum irradiated through one of said incident paths and reflected from said skin being analyzed to determine said skin thickness parameter in order to select one of said different incident paths assigned to one of said groups identified by the determined skin thickness,
said NIR spectrum data being processed by use of the calibrating equation specific to one of said groups determined by said skin thickness parameter, when the selected incident path corresponds with the incident path which directed the light having the NIR spectrum to the skin to determine the skin thickness parameter,
said selected incident path being made active to direct said light having the NIR spectrum to said skin so as to obtain said NIR spectrum data from said NIR spectrum reflected from said skin, said NIR spectrum data being processed by use of the calibrating equation specific to one of said groups determined by said skin thickness parameter, when the selected incident path does not correspond with the incident path which directed the light having the NIR spectrum to the skin to determine the skin thickness parameter.

5. The method as set forth in claim 4, wherein said skin thickness parameter is determined by statistically analyzing said NIR (near infrared) spectrum reflected from the skin of the subject.

6. The method as set forth in claim 5, wherein said NIR (near infrared) spectrum is analyzed based upon a principal component analysis.

7. The method as set forth in claim 4, wherein the biological component density is glucose density.

* * * * *